United States Patent [19]

Saikawa et al.

[11]  4,312,986

[45]  Jan. 26, 1982

[54] PROCESS FOR PRODUCING 7-(SUBSTITUTED)AMINO-3-SUBSTITUTED THIOMETHYL-$\Delta^3$-CEPHEM-4-CARBOXYLIC ACIDS

[75] Inventors: Isamu Saikawa; Shuntaro Takano, both of Toyama; Kaishu Momonoi, Shinminato; Isamu Takakura, Toyama; Seietsu Kuroda, Toyama; Kiyoshi Tanaka, Toyama; Kenshin Hayashi, Tonami; Bunei Nagahashi, Toyama; Chiaki Kutani, Funabashi, all of Japan

[73] Assignee: Toyama Chemical Co., Ltd., Tokyo, Japan

[21] Appl. No.: 54,917

[22] Filed: Jul. 5, 1979

[30] Foreign Application Priority Data

Jul. 6, 1978 [JP] Japan .................................. 53-82377

[51] Int. Cl.³ ........................................... C07D 501/04
[52] U.S. Cl. ...................................... 544/26; 544/27; 424/246; 544/21; 542/420
[58] Field of Search ....................... 544/27, 28, 26, 21, 544/30; 542/420

[56] References Cited

U.S. PATENT DOCUMENTS

| 3,261,832 | 7/1966 | Couley et al. | 260/243 C |
| 3,516,997 | 6/1970 | Takano et al. | 260/243 C |
| 3,833,572 | 4/1974 | Clark et al. | 544/17 |
| 3,840,531 | 10/1974 | Greene | 260/243 C |
| 3,872,115 | 3/1975 | Sugimoto et al. | 544/27 |
| 4,014,874 | 3/1977 | Peter et al. | 544/27 |
| 4,144,391 | 3/1979 | Hatfield | 544/27 |
| 4,150,156 | 4/1979 | Beattie et al. | 544/17 |

FOREIGN PATENT DOCUMENTS

| 2332045 | 1/1974 | Fed. Rep. of Germany . |
| 2065621 | 9/1974 | Fed. Rep. of Germany . |
| 1795484 | 9/1974 | Fed. Rep. of Germany . |
| 2530622 | 1/1976 | Fed. Rep. of Germany . |
| 1400804 | 7/1975 | United Kingdom . |

OTHER PUBLICATIONS

Central Patents Index Week V28, Aug. 16, 1973.
Central Patents Index Week V48, Jan. 3, 1974.
Central Patents Index Week V3, Feb. 21, 1974.
Central Patents Index Week V12, Apr. 30, 1974.
Central Patents Index Week V25, Jul. 30, 1974.
Central Patents Index Week V38, Oct. 29, 1974.
Central Patents Index Week V39, Nov. 5, 1974.
Central Patents Index Week V49, Jan. 14, 1975.
Central Patent Index Week W7, Mar. 25, 1979.
Central Patent Index Week X6, Mar. 16, 1976.
Central Patent Index Week X40, Nov. 10, 1976.
Cocker et al., J. Chem. Soc., pp. 5015–5031 (1965).
Taylor, J. Chem. Soc., pp. 7020–7029 (1965).

Primary Examiner—Nicholas S. Rizzo
Attorney, Agent, or Firm—Oblon, Fisher, Spivak, McClelland & Maier

[57] ABSTRACT

This disclosure relates to a novel process for producing 7-(substituted)-amino-3-substituted thiomethyl-$\Delta^3$-cephem-4-carboxylic acids which are intermediate products of cephalosporins being valuable antibacterial compounds for use in mammals including man.

23 Claims, No Drawings

PROCESS FOR PRODUCING 7-(SUBSTITUTED)AMINO-3-SUBSTITUTED THIOMETHYL-Δ³-CEPHEM-4-CARBOXYLIC ACIDS

This invention relates to a novel process for producing 7-(substituted)amino-3-substituted thiomethyl-Δ³-cephem-4-carboxylic acids.

Many publications, for example, German Offenlegungsschrift Nos. 1,795,484; 2,018,600; and 2,065,621, U.S. Pat. No. 3,516,997, and Japanese Patent Application Kokai (Laid-Open) No. 154,287/75, report reacting a thiol compound or its salt with the acetoxy group in the 3-position of a 7-aminocephalosporanic acid or a derivative in the carboxyl group thereof or a salt thereof to convert the acetoxy group in the 3-position. Said publications disclose that it is not desirable to effect said reaction in an organic solvent free from water and it is preferable to effect the reaction in water or a mixture of water and an organic solvent at a pH of 6 to 7. However, even under said preferably reaction conditions, the product obtained is extremely impure and the yield is 30 to 50%. The present inventors' duplication of said reaction has clarified that the yield is 30 to 50% at most and the product is in admixture with the starting 7-aminocephalosporanic acid. On the other hand, U.S. Pat. No. 3,840,531; Japanese Patent Application Kokai (Laid-Open) Nos. 295/74 and 10,077/73, German Offenlegungsschrift Nos. 2,332,045, Japanese Patent Publication No. 13,023/71 and the like report a method for smoothly carrying out the conversion in the 3-position by which a 7-aminocephalosporanic acid or its salt, the amino group in the 7-position of which has been protected with an acyl group, such as formyl, lower alkanoyl or the like, or cephalosporin C or a derivative thereof is used as the starting material. However, said publications describe that even according to said method, it is preferable to carry out the reaction in water or a mixture of water and an organic solvent in the vicinity of neutral.

Concerning a method by which a cephalosporin C derivative is used as the starting material, it is reported in, for example, British Pat. No. 1,400,804, and Japanese Patent Application Kokai (Laid-Open) No. 95,088/76, that the conversion in the 3-position is effected in water or a mixture of water and an organic solvent in the presence of a halide or inorganic salt of a metal of Group I or II of the Periodic Table, such as KI, NaI, CaI₂, BaI₂, NaCl, NH₄Cl, BaCl₂, MgCl₂ or the like. However, the method by which an acylated cephalosporanic acid, cephalosporin C or its derivative is used as the starting material is complicated in reaction because the amino group in the 7-position must be acylated, or an acylated starting material must be used and the acyl group must be removed by iminohalogenation, iminoetherification, hydrolysis or the like after the conversion in the 3-position. In said reaction, the conversion per se in the 3-position with a thiol or its salt is effected in a mixture of water and an organic solvent under the above-mentioned preferable conditions, and in general, the yield is 60 to 80%.

On the above-mentioned background, the present inventors have conducted extensive research with an intention of developing a method for converting the group in the 3-position with a thiol compound or its salt in a high yield with ease in industry, and consequently, have unexpectedly found that when the reaction is effected in an organic solvent in the presence of a protonic acid or a Lewis acid or complex compound of Lewis acid other than boron trifluoride and its complex compounds, a satisfactory result is obtained.

An object of this invention is to provide a process for producing a 7-(substituted)amino-3-substituted thiomethyl-Δ³-cephem-4-carboxylic acid or a derivative in the carboxyl group thereof or a salt thereof which is important as an intermediate of a cephalosporin compound from a cephalosporanic acid or a derivative in the carboxyl group thereof in a high yield and a high purity by means of an industrially easy operation.

Other objects and advantages of this invention will be apparent from the following description.

According to this invention, there is provided a process for producing a 7-(substituted)amino-3-substituted thiomethyl-Δ³-cephem-4-carboxylic acid represented by the general formula (I),

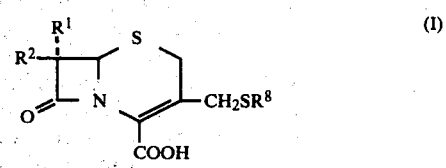

wherein $R^1$ is a hydrogen atom or a $C_{1-14}$ alkoxy group; $R^2$ is an amino group or a group represented by the formula,

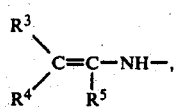

in which $R^3$, $R^4$, and $R^5$, which may be identical or different, are hydrogen or organic residues which do not participate in the reaction, or by the formula,

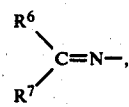

in which $R^6$ and $R^7$, which may be identical or different, are hydrogen or organic residues which do not participate in the reaction; and $R^8$ is a thiol compound residue, a derivative in the carboxyl group of the above carboxylic acid or a salt thereof, which comprises reacting a cephalosporanic acid represented by the general formula (II),

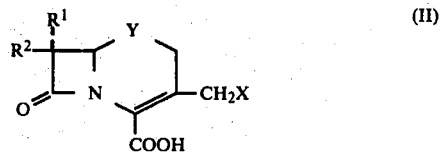

wherein $R^1$ and $R^2$ are the same as defined above; X is an unsubstituted or substituted acyloxy or carbamoyloxy group; >Y is >S or >S→O, or a derivative in the carboxyl group of said cephalosporanic acid, or a salt thereof, with a thiol compound represented by the general formula (III),

 

wherein $R^8$ has the same meaning as defined above, or a salt of the thiol compound, in an organic solvent in the presence of a protonic acid, or a Lewis acid or complex compound of Lewis acid other than boron trifluoride and its complex compounds. There can be used not only a compound having $>Y$ being $>S$ but also a chemically stable compound having $>Y$ being $>S\rightarrow O$ as the starting material. In the latter case, reduction reaction of $>S\rightarrow O$ takes place owing to the presence of a protonic acid, or a Lewis acid or complex compound of Lewis acid other than boron trifluoride and its complex compounds, thereby obtaining a compound having $>Y$ being $>S$.

As the $C_{1-4}$alkoxy group for $R^1$ in the general formulas (I) and (II) mentioned above, there may be exemplified methoxy, ethoxy, propoxy, butoxy and the like.

As the unsubstituted or substituted acyloxy or carbamoyloxy group for X in the general formula (II), there may be exemplified $C_{1-8}$alkanoyloxy groups, for example, formyloxy, acetoxy, propionyloxy, butyryloxy and the like; $C_{3-8}$alkenoyloxy groups, for example, acryloyloxy and the like; $C_{7-11}$aroyloxy groups, for example, benzoyloxy, naphthoyloxy, and the like; $C_{8-9}$aralkanoyloxy groups, for example, phenylacetoxy, phenylpropionyloxy and the like; carbamoyloxy groups; and the like, of which $C_{1-8}$acyloxy groups and carbamoyloxy groups are preferable. As the substituent of the substituted acyloxy or carbamoyloxy group, there may be exemplified known substituents for acyloxy and carbamoyloxy groups, such as halogen, nitro, $C_{1-4}$alkyl, $C_{1-4}$alkoxy, $C_{1-4}$alkylthio, $C_{1-8}$acyl, $C_{1-8}$acyloxy, $C_{1-8}$acylamino, hydroxyl, carboxyl, sulfamoyl, carbamoyl, cyano, carboxy-$C_{1-4}$alkoxycarbamoyloxy, benzoylcarbamoyl, carboxy-$C_{1-4}$alkoxysulfamoyl, and the like.

In the general formulas (I) and (II), $R^2$ is an amino group or a group represented by the formula,

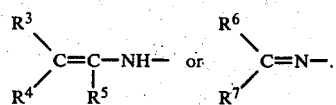

The formula

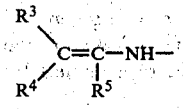

may also be rewritten

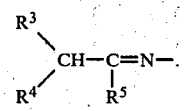

as an isomer, and the latter is also included in this invention.

As the organic residues for $R^3$, $R^4$, $R^5$, $R^6$ and $R^7$ which do not participate in the reaction, there may be used those known in this field, and examples thereof are unsubstituted or substituted aliphatic residues, alicyclic residues, aromatic residues, araliphatic residues, heterocyclic residues, acyl groups and the like. More specifically, the following groups may be exemplified:

(1) Aliphatic residue: alkyl groups, for instance, methyl, ethyl, propyl, butyl, isobutyl, pentyl and the like; and alkenyl groups, for instance, vinyl, propenyl, butenyl and the like.

(2) Alicyclic residue: cycloalkyl groups, for instance, cyclopentyl, cyclohexyl, cycloheptyl and the like; and cycloalkenyl groups, for instance, cyclopentenyl, cyclohexenyl and the like.

(3) Aromatic residue: aryl groups, for instance, phenyl, naphthyl and the like.

(4) Araliphatic residue: aralkyl groups, for instance, benzyl, phenethyl and the like.

(5) Heterocyclic residue: heterocyclic groups containing one or more hetero atoms (oxygen, nitrogen and sulfur) in any combination in any position in the molecule, for instance, pyrrolidyl, piperazinyl, furyl, thienyl, pyrrolyl, pyrazolyl, oxazolyl, thiazolyl, pyridyl, imidazolyl, quinolyl, benzothiazolyl, oxadiazolyl, thiadiazolyl, triazolyl, tetrazolyl and the like.

(6) Acyl group: acyl groups derived from organic carboxylic acids. As said organic carboxylic acids, there may be exemplified aliphatic carboxylic acids; alicyclic carboxylic acids; alicycloaliphatic carboxylic acids; araliphatic carboxylic acids, aromatic oxy aliphatic carboxylic acids, aromatic thio aliphatic carboxylic acids, heterocyclic ring-substituted aliphatic carboxylic acids, heterocyclic oxy aliphatic carboxylic acids, and heterocyclic thio aliphatic carboxylic acids, in which an aromatic residue or heterocyclic group is bonded to an aliphatic carboxylic acid directly or through an oxygen or sulfur atom; organic carboxylic acids in which an aromatic ring, an aliphatic group or an alicyclic group is bonded to the carbonyl group through an oxygen, nitrogen or sulfur atom; aromatic carboxylic acids; and heterocyclic carboxylic acids.

As the above aliphatic carboxylic acids, there may be exemplified formic acid, acetic acid, propionic acid, butanoic acid, isobutanoic acid, pentanoic acid, methoxyacetic acid, methylthioacetic acid, acrylic acid, crotonic acid and the like. As the above alicyclic carboxylic acids, there may be exemplified cyclohexanoic acid and the like, and as the above alicycloaliphatic carboxylic acids, there may be exemplified cyclopentaneacetic acid, cyclohexane-acetic acid, cyclohexane-propionic acid, cyclohexadiene-acetic acid and the like. As the aromatic residue in the above organic carboxylic acids, there may be exemplified phenyl, naphthyl, and the like, and as the heterocyclic residue, there may be exemplified residues of heterocyclic compounds containing at least one hetero atom in the ring, such as furane, thiophene, pyrrole, pyrazole, imidazole, triazole, thiazole, isothiazole, oxazole, isoxazole, thiadiazole, oxadiazole, thiatriazole, oxatriazole, tetrazole, benzoxazole, benzofuran and the like.

Each of the groups constituting the above organic carboxylic acid may be further substituted by a substituent, for example, a halogen atom, a hydroxyl group, a protected hydroxyl group, a $C_{1-5}$alkyl group, a $C_{1-5}$alkoxy group, a $C_{1-4}$acyl group, a nitro group, an amino group, a protected amino group, a mercapto group, a protected mercapto group, a carboxyl group, a protected carboxyl group or the like.

As the protecting groups in the abovementioned protected hydroxyl, protected amino, protected mercapto and protected carboxyl groups, there may be used those which will be mentioned hereinafter concerning substituents in the $R^8$ group.

$R^3$, $R^4$ and $R^5$ may be identical or different, and are preferably hydrogen, $C_{1-5}$alkyl, $C_{2-4}$alkenyl, $C_{5-7}$cycloalkyl, $C_{5-7}$cycloalkenyl, aryl, aralkyl, heterocyclic containing O, N and S alone or in any combination in any position, or acyl, and $R^6$ and $R^7$ may be identical or different, and are preferably hydrogen, $C_{1-5}$alkyl, $C_{2-4}$alkenyl, $C_{5-7}$cycloalkyl, $C_{5-7}$cycloalkenyl, aryl, aralkyl, heterocyclic containing O, N, and S alone or in any combination in any position, or acyl.

As the derivatives in the carboxyl group of the compounds represented by the general formulas (I) and (II), there may be exemplified derivatives known usually in the field of penicillin and cephalosporin, for example, the following compounds:

(a) Esters: all esters which do not affect the reaction at all are included, for example, substituted or unsubstituted alkyl esters, such as methyl ester, ethyl ester, propyl ester, isopropyl ester, butyl ester, tert.-butyl ester, methoxymethyl ester, ethoxymethyl ester, phenoxymethyl ester, methylthiomethyl ester, methylthioethyl ester, phenylthiomethyl ester, dimethylaminoethyl ester, diethylaminoethyl ester, morpholinoethyl ester, piperidinoethyl ester, acetylmethyl ester, phenacyl ester, toluoylmethyl ester, 4-nitrophenacyl ester, acetoxymethyl ester, pivaloyloxymethyl ester, benzoyloxymethyl ester, 1,1-diacetylmethyl ester, 1-acetyl-1-methoxycarbonylmethyl ester, methanesulfonylethyl ester, toluenesulfonylethyl ester, bromomethyl ester, iodoethyl ester, trichloroethyl ester, cyanomethyl ester, thenoylmethyl ester, phthalimidomethyl ester and the like; cycloalkyl esters, such as cyclohexyl ester, cycloheptyl ester and the like; alkenyl esters, such as propenyl ester, allyl ester, 3-butenyl ester and the like; alkinyl esters, such as propinyl ester and the like; substituted or unsubstituted aryl esters, such as phenyl ester, tolyl ester, xylyl ester, naphthyl ester, p-nitrophenyl ester, 2,4-dinitrophenyl ester, p-methoxyphenyl ester, trichlorophenyl ester, pentachlorophenyl ester, p-methanesulfonylphenyl ester and the like; substituted or unsubstituted aralkyl esters, such as benzyl ester, phenethyl ester, p-chlorobenzyl ester, p-nitrobenzyl ester, p-methoxybenzyl ester, 3,5-dimethoxybenzyl ester, diphenylmethyl ester, bis(4-methoxyphenyl)methyl ester, 3,5-di-tert.-butyl-4-hydroxybenzyl ester, trityl ester and the like; indanyl ester; phthalidyl ester; other esters formed from a carboxylic acid and thioalcohol, tetrahydrofuranol, 1-cyclopropylethanol, 1-phenyl-3-methyl-5-pyrazolone, 3-hydroxypyridine, 2-hydroxypyridine-1-oxide or the like, which may be optionally substituted by a halogen atom, a nitro group, an alkoxy group or the like; and esters formed by reaction between a carboxylic acid and methoxyacetylene, ethoxyacetylene, tert.-butylethinyldimethylamine, ethylethinyldiethylamine, or N-ethyl-5-phenylisoxazolium-3-sulfonic acid salt.

(b) Anhydrides of the carboxyl group with N-hydroxysuccinic acid imide, N-hydroxyphthalic acid imide, dimethylhydroxylamine, diethylhydroxylamine, 1-hydroxypiperidine, oxime or the like.

(c) Amides: all of acid amides, N-substituted acid amides, and N,N-di-substituted acid amides are included, for example, N-alkyl acid amides, such as N-methyl acid amide, N-ethyl acid amide and the like; N-aryl acid amides, such as N-phenyl acid amide and the like; N,N-dialkyl acid amides, such as N,N-dimethyl acid amide, N,N-diethyl acid amide, N-ethyl-N-methyl acid amide and the like; and acid amides with imidazole, 4-substituted imidazole, triazolopyridone and the like.

The salt in the term "a compound of the general formula (I) or (II), or a derivative in the carboxyl group thereof or a salt thereof" used in the specification and claims means to include both salt at the acidic group (for example, carboxyl group) and salt at the basic group (for example, amino group). As the salt at the acidic group, there may be exemplified salts with alkali metals such as sodium, potassium and the like; salts with alkaline earth metals such as calcium, magnesium and the like; ammonium salts, salts with nitrogen-containing organic bases such as triethylamine, diethylamine, pyridine, N-methylpiperidine, N-methylmorpholine, N,N-dimethylaniline and the like. As the salt at the basic group, there may be exemplified salts with mineral acids, such as hydrochloric acid, sulfuric acid and the like; salts with organic acids such as oxalic acid, formic acid, trichloracetic acid; trifluoroacetic acid and the like; and salts with sulfonic acids, such as methanesulfonic acid, toluenesulfonic acid, naphthalenesulfonic acid and the like. These salts may be previously prepared and isolated or may be prepared in the reaction system. Hydrates of the starting and objective compounds mentioned above are also included in this invention.

$R^8$ in the general formulas (I) and (III) represents residues of thiol compounds known in the field of cephalosporin, and includes, for example, unsubstituted or substituted alkyl, cycloalkyl, aryl, aralkyl, acyl, thiocarbamoyl, alkoxythiocarbonyl, aryloxythiocarbonyl, cycloalkyloxythiocarbonyl, amidino, and heterocyclic groups. More specifically, there may be exemplified $C_{1-8}$alkyl, such as methyl, ethyl, propyl, butyl, isobutyl and the like; $C_{5-7}$-cycloalkyl, such as cyclohexyl, cycloheptyl and the like; $C_{7-9}$aralkyl, such as benzyl, phenethyl, and the like; aryl, such as phenyl, naphthyl and the like; acyl, such as acetyl, propionyl, butyryl, benzoyl, naphthoyl, cyclopentanecarbonyl, cyclohexanecarbonyl, furoyl, thenoyl, isothiazolylcarbonyl, isoxazolylcarbonyl, thiadiazolylcarbonyl, triazolylcarbonyl and the like; thiocarbamoyl, such as thiocarbamoyl, N-methylthiocarbamoyl, N,N-diethylthiocarbamoyl, 1-piperidinothiocarbonyl, 1-morpholinothiocarbonyl, 4-methyl-1-piperazinylthiocarbonyl, and the like; $C_{1-4}$alkoxythiocarbonyl, such as methoxythiocarbonyl, ethoxythiocarbonyl, propoxythiocarbonyl, butoxythiocarbonyl and the like; aryloxythiocarbonyl, such as phenoxythiocarbonyl and the like; $C_{5-7}$cycloalkyloxythiocarbonyl, such as cyclohexyloxythiocarbonyl and the like; amidino, such as amidino, N-methylamidino, N,N'-dimethylamidino, and the like; and heterocyclic groups, such as oxazolyl, thiazolyl, isoxazolyl, isothiazolyl, imidazolyl, pyrazolyl, pyridyl, pyrazinyl, pyrimidinyl, pyridazinyl, quinolyl, isoquinolyl, quinazolyl, indolyl, indazolyl, oxadiazolyl, thiadiazolyl, triazolyl, thiatriazolyl, tetrazolyl, triazinyl, benzimidazolyl, benzoxazolyl, benzothiazolyl, triazolopyridyl, purinyl, pyridine-1-oxide-2-yl, pyridazine-1-oxide-6-yl, tetrazolopyridazinyl, tetrazalopyridazinyl, thiazolopyridazinyl, thiadiazolopyridazinyl, triazolopyridazinyl, and the like. As the heterocyclic group for $R^8$, nitrogen-containing heterocyclic groups which contain at least one nitrogen atom with or without oxygen or sulfur atom are preferable.

Furthermore, the groups for $R^8$ may be substituted by at least one substituent, such as halogen, $C_{1-4}$alkyl, phenyl, hydroxyl, mercapto, $C_{1-4}$alkoxy, $C_{1-4}$alkylthio, nitro, cyano, cyano-$C_{1-4}$alkyl, amino, $C_{1-4}$alkylamino, di-$C_{1-4}$alkylamino, $C_{1-8}$acylamino, $C_{1-8}$acyl, $C_{1-8}$acyloxy, carboxyl, carbamoyl, amino-$C_{1-4}$alkyl, N-$C_{1-4}$alkylamino-$C_{1-4}$alkyl, N,N-di-$C_{1-4}$-alkylamino-$C_{1-4}$alkyl, hydroxy-$C_{1-4}$alkyl, $C_{1-4}$alkoxy-$C_{1-4}$alkyl, carboxyl-$C_{1-4}$alkyl, sulfo-$C_{1-4}$alkyl, sulfo, sulfamoyl-$C_{1-4}$alkyl, sulfamoyl, carbamoyl-$C_{1-4}$alkyl, $C_{2-4}$alkenyl, carbamoyl-$C_{2-4}$alkenyl, N-$C_{1-4}$alkyl-carbamoyl, N,N-di-$C_{1-4}$alkylcarbamoyl, $C_{1-8}$acyl-$C_{1-4}$-alkyl, N-$C_{1-4}$alkylcarbamoyl-$C_{1-4}$alkyl, N,N-di-$C_{1-4}$-alkylcarbamoyl-$C_{1-4}$alkyl, and the like, and among these substituents, the hydroxyl, mercapto, amino and carboxyl groups may be protected with an appropriate protecting group which is usually used in the field of penicillin or cephalosporin. The protecting group for the amino group includes all groups which can be used as common amino-protecting groups, for example, trichloroethoxycarbonyl, tribomoethoxycarbonyl, benzyloxycarbonyl, p-toluenesulfonyl, p-nitrobenzyloxycarbonyl, o-bromobenzyloxycarbonyl, o-nitrophenylsulfenyl, chloroacetyl, trifluoroacetyl, formyl, tert.-butoxycarbonyl, p-methoxybenzyloxycarbonyl, 3,4-dimethoxybenzyloxycarbonyl, 4-(phenylazo)benzyloxycarbonyl, 4-(4-methoxyphenylazo)benzyloxycarbonyl, pyridine-1-oxide-2-ylmethoxycarbonyl, 2-pyridylmethoxycarbonyl, 2-furyloxycarbonyl, diphenylmethoxycarbonyl, 1,1-dimethylpropoxycarbonyl, isopropoxycarbonyl, 1-cyclopropylethoxycarbonyl, phthaloyl, succinyl, 1-adamanthyloxycarbonyl, 8-quinolyloxycarbonyl and the like, which are easily removable acyl groups; other easily removable groups such as trityl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxycyclohexylidene and the like; and di- or tri-alkylsilyl.

The protecting groups for the hydroxyl and mercapto groups include all groups that can usually be used as protecting groups for hydroxyl and mercapto groups, for example easily removable acyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, 4-(phenylazo)-benzyloxycarbonyl, 4-(4-methoxyphenylazo)benzyloxycarbonyl, tert.-butoxycarbonyl, 1,1-dimethylpropoxycarbonyl, isopropoxycarbonyl, diphenylmethoxycarbonyl, 2-pyridylmethoxycarbonyl, 2,2,2-trichloroethoxycarbonyl, 2,2,2-tribromoethoxycarbonyl, 2-furfuryloxycarbonyl, 1-adamantyloxycarbonyl, 1-cyclopropylethoxycarbonyl, 3-quinolyloxycarbonyl, trifluoroacetyl and the like; benzyl; trityl; methoxymethyl; 2-nitrophenylthio; 2,4-dinitrophenylthio and the like.

The protecting group for the carboxyl group include all groups that can usually be used as carboxyl-protecting groups, for example, ester-forming groups, such as methyl, ethyl, propyl, isopropyl, tert.-butyl, butyl, benzyl, diphenylmethyl, triphenylmethyl, p-nitrobenzyl, p-methoxybenzyl, benzoylmethyl, acetylmethyl, p-nitrobenzoylmethyl, p-bromobenzoylmethyl, p-methanesulfonylbenzoylmethyl, phthalimidomethyl, trichloroethyl, 1,1-dimethyl-2-propinyl, acetoxymethyl, propionyloxymethyl, pivaloyloxymethyl, 1,1-dimethylpropyl, 1,1-dimethyl-2-propenyl, 3-methyl-3-butenyl, succinimidomethyl, 1-cyclopropylethyl, methylsulfenylmethyl, phenylsulfenylmethyl, methylthiomethyl, phenylthiomethyl, dimethylaminomethyl, quinoline-1-oxide-2-yl-methyl, pyridine-1-oxide-2-yl-methyl, di-(p-methoxyphenyl)methyl and the like; silyl residues of silyl compounds disclosed in Japanese Patent Application Kokai (Laid-Open) No. 7073/71 and Dutch Patent Application No. 7105259 (already laid open to public inspection), such as dimethyldichlorosilane; non-metallic residues of non-metallic compounds disclosed in German Offenlegungsschrift No. 2,062,925, such as titanium tetrachloride; and the like.

Salts of the thiol compound represented by the general formula (III) may be in the basic salt form or in the acidic salt form depending upon the type of $R^8$ and include both the basic and acidic salts. As to examples of the salt, the explanation of the salt of the compounds represented by the general formulas (I) and (II) mentioned above applies. As the material for forming the salt of the thiol compound, there may be used the materials for forming the salts of the compounds represented by the general formulas (I) and (II).

As the protonic acids, there may be exemplified pyrophosphoric acid, pyrosulfuric acid, sulfuric acids, sulfonic acids and super acids. The term "super acid" used herein means acids stronger than 100% sulfuric acid and includes a part of the sulfonic acids and sulfuric acids. More specifically, the sulfuric acids include sulfuric acid, chlorosulfuric acid, fluorosulfuric acid and the like, and the sulfonic acids include alkyl-(mono- or di-) sulfonic acids such as methanesulfonic acid, trifluoromethanesulfonic acid and the like and aryl-(mono-, di- or tri-)sulfonic acids such as benzenesulfonic acid, naphthalenesulfonic acid, p-toluenesulfonic acid and the like. The super acids include perchloric acid, magic acid($FSO_3H$—$SbF_5$), $FSO_3H$—$AsF_5$, $CF_3SO_3H$—$SbF_5$, $H_2SO_4$—$SO_3$ and the like. The Lewis acids other than boron trifluoride include, for example, zinc halides and tin halides, and more specifically include zinc chloride, zinc bromide, stannic chloride, stannic bromide and the like. The complex compounds of Lewis acids other than complex compounds of boron trifluoride include complex salts of the above-mentioned Lewis acids other than boron trifluoride with dialkyl ethers such as diethyl ether, di-n-propyl ether, di-n-butyl ether and the like; complex salts of the above-mentioned Lewis acids with amines such as ethylamine, n-propylamine, n-butylamine, triethanolamine, dimethylformamide and the like; complex salts of the above-mentioned Lewis acids with fatty acids such as acetic acid, propionic acid and the like; complex salts of the above-mentioned Lewis acids with nitriles, such as acetonitrile, propionitrile and the like; complex salts of the above-mentioned Lewis acids with carboxylic esters such as methyl formate, ethyl formate, ethyl acetate and the like; and complex salts of the above-mentioned Lewis acids with phenols, such as phenol, (1- or 2-)naphthol and the like. The above-mentioned sulfonic acids may be substituted by halogen atoms such as fluorine, chlorine, bromine and the like, carboxyl groups, sulfo groups, nitro groups, lower alkyl groups such as methyl, ethyl and the like or lower alkoxy groups such as methoxy, ethoxy and the like.

The compound represented by the general formula (II) in which $R^2$ is

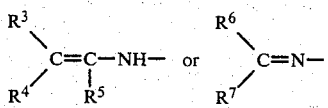

in which $R^3$, $R^4$, $R^5$, $R^6$ and $R^7$ are the same as defined above can be synthesized by reacting 7-aminocephalosporanic acid with an aldehyde or a ketone in an inert solvent (Japanese Patent Publication No. 28,913/69), and the compound represented by the general formula (II) wherein $R^1$ is a $C_{1-4}$alkoxy group can be synthesized by introducing the $C_{1-4}$alkoxy group into the compound represented by the general formula (II) in which $R^1$ is a hydrogen atom in a manner known per se (Journal of Synthetic Organic Chemistry, Japan, 35, 563–574 (1977), etc.).

As the organic solvent used in the process of this invention, there may be used all organic solvents which do not adversely affect the reaction, and preferable are nitriles, nitroalkanes, organic carboxylic acids, ketones, ethers and sulfolanes. These solvents may be used in admixture of two or more. The above nitriles include, for example, aliphatic nitriles, aliphatic dinitriles, aromatic nitriles, and heterocyclic nitriles, such as acetonitrile, propionitrile, butyronitrile, isobutyronitrile, valeronitrile, isovaleronitrile, capronitrile, enanthonitrile, caprylonitrile, pelargononitrile, caprinitrile, crotononitrile, lauronitrile, palmitonitrile, stearonitrile, acrylonitrile, malononitrile, succinonitrile, glutaronitrile, adiponitrile, benzonitrile, tolunitrile, benzyl cyanide, cinnamonitrile, naphthonitrile, cyanothiophene, and the like. The nitroalkanes include nitromethane, nitroethane, nitropropane, nitrobutane, nitropentane, nitrohexane, nitroheptane, nitrooctane and the like. The organic carboxylic acids include aliphatic saturated monocarboxylic acids and aliphatic saturated dicarboxylic acids, such as formic acid, acetic acid, propionic acid, lactic acid, isolatic acid, valeric acid, isovaleric acid, pivalic acid, trifluoroacetic acid and the like. The ketones include aliphatic saturated ketones, aliphatic unsaturated ketones, alicyclic ketones, aromatic ketones, and heterocyclic ketons, such as acetone, ethyl methyl ketone, methyl propyl ketone, isopropyl methyl ketone, butyl methyl ketone, isobutyl methyl ketone, diethyl ketone, diisopropyl ketone, mesityl oxide, methylheptenone, cyclobutanone, cyclopentanone, cyclohexanone, acetophenone, propiophenone, butyrophenone, valerophenone, dibenzyl ketone, acetothienone, 2-acetofurone, and the like. The ethers include aliphatic saturated ethers, aliphatic unsaturated ethers, aromatic ethers, and cyclic ethers such as diethyl ether, dipropyl ether, diisopropyl ether, dibutyl ether, diisobutyl ether, methyl ethyl ether, methyl propyl ether, methyl isopropyl ether, methyl butyl ether, methyl isobutyl ether, ethyl propyl ether, ethyl isopropyl ether, ethyl butyl ether, ethyl isobutyl ether, ethylene glycol dimethyl ether, diallyl ether, methyl allyl ether, ethyl allyl ether, anisole, phenetole, dibenzyl ether, phenyl benzyl ether, tetrahydrofuran, tetrahydropyran, dioxane and the like. The sulfolanes include sulfolane and the like. The organic solvent used in this invention may form a complex with said Lewis acid other than boron trifluoride, and this organic solvent complex with said Lewis acid other than boron trifluoride is also used as the organic solvent in this invention.

The amount of the protonic acid or the Lewis acid or complex compound of Lewis acid other than boron trifluoride and its complex compounds used may be at least one mole per mole of the compound represented by the general formula (II), or a derivative in the carboxyl group thereof or a salt thereof, and preferably at least 2 moles, particularly 2 to 10 moles, per mole of the latter. When the complex compound is used, it may also be used as a solvent, and a mixture of two or more complex compounds may also be used. In general, it is desirable to vary the amount of the protonic acid or the Lewis acid or complex compound of Lewis acid other than boron tirfluoride and its complex compounds in order to control the reaction rate depending upon the type of solvent and thiol compound or its salt used. The amount of the thiol compound represented by the general formula (III) or its salt used is generally at least one mole per mole of the compound represented by the general formula (II) or a derivative in the carboxyl group thereof or a salt thereof, and preferably 1 to 1.5 moles per mole of the latter. When the compound having $>Y$ being $>S \rightarrow O$ is used as the starting material, the thiol compound or its salt is preferably used in an amount of 2 to 3 moles per mole of the starting material.

Although no particular limitation is applied to the reaction temperature, the reaction is generally effected at a temperature of $-20°$ to $80°$ C., and the reaction time is generally several minutes to scores of hours.

In the process of this invention, the following dehydrating agents may be added to the reaction system: phosphorus compounds such as phosphorus pentachloride, polyphosphoric acid, phosphorus pentoxide, phosphorus trichloride, phosphorus oxychloride and the like; organic silyl compounds such as N,O-bis(trimethylsilyl)-acetamide, trimethylsilylacetamide, trimethylchlorosilane, dimethyldichlorosilane and the like; organic acid chlorides, such as acetyl chloride, p-toluenesulfonyl chloride and the like; acid anhydrides, such as acetic anhydride, trifluoroacetic anhydride, and the like; and inorganic compounds for drying, such as anhydrous magnesium sulfate, anhydrous calcium chloride, anhydrous calcium sulfate, molecular sieves, calcium carbide and the like.

The above-mentioned reaction conditions are not limitative and can appropriately be varied depending upon the type of reactants and solvents to achieve the object. The protecting group

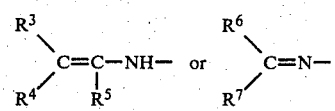

For $R^2$ in the general formula (I) and the protecting group for the carboxyl group in the derivative in the carboxyl group of the compound represented by the general formula (I) can generally be removed by hydrolysis or treatment in a conventional manner to convert the protected groups into an amino group and carboxyl group, respectively. However, in the case where some groups of

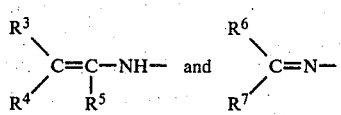

are used or where a certain after-treatment is used the protecting group for amino group is easily removed during the treatment to obtain a compound represented by the general formula (I) in which $R^2$ is an amino group. In the case where the carboxyl group of the compound represented by the general formula (I) is protected with some protecting groups or where a certain after-treatment is used, the protecting group is easily removed during the treatment to convert the protected carboxyl group into a carboxyl group to obtain a compound represented by the general formula (I). When $R^3$, $R^4$, $R^5$, $R^6$ and $R^7$ are organic residues which do not participate in the reaction and which have a protected hydroxyl, amino, mercapto or carboxyl group as substituent, these groups can be converted into the desired substituents by subjecting the resulting compound to removal reaction in a conventional manner. The protecting group-removal reaction mentioned above may be effected without isolating the resulting product. The objective compound thus obtained having the general formula (I) can be isolated in a conventional manner.

The objective compound represented by the general formula (I) can directly be used as the starting material for acylation reaction, however it can, if necessary, be converted into highly pure 7-(substituted)-amino-3-substituted thiomethyl-$\Delta^3$-cephem-4-carboxylic acid in a high yield in a conventional manner.

The following Examples illustrate this invention, but it should be understood that the Examples are merely by way of illustration and not by way of limitation.

EXAMPLE 1

(1) In 27 ml of acetic acid were suspended 2.72 g of 7-aminocephalosporanic acid and 1.16 g of 5-mercapto-1-methyl-1H-tetrazole, and 5.76 g of methanesulfonic acid was added to the suspension to form a solution. This solution was subjected to reaction at 50° C. for 2.5 hrs. After the completion of the reaction, the reaction mixture was cooled and gradually added to 27 ml of water with ice-cooling. Subsequently, the mixture was adjusted to a pH of 4.0 with 28% by weight aqueous ammonia. The thus precipitated crystals were collected by filtration, washed with 5 ml of water and 5 ml of acetone in this order, and thereafter dried to obtain 2.70 g (yield 82.3% of 7-amino-3-[5-(1-methyl-1,2,3,4-tetrazolyl)thiomethyl]-$\Delta^3$-cephem-4-carboxylic acid having a melting point of 224° to 226° C. (decomp.).

IR (KBr) cm$^{-1}$: $\nu_{C=O}$ 1792, 1610, 1520.

NMR (D$_2$O+CF$_3$CO$_2$D) ppm values: 3.58 (2H, s, C$_2$—H$_2$), 3.84 (3H, s,>N—CH$_3$), 4.09 (2H, s, C$_3$—CH$_2$), 4.91 (1H, d, J=5 cps, C$_6$—H), 5.05 (1H, d, J=5 cps, C$_7$—H).

Elementary analysis for C$_{10}$H$_{12}$N$_6$O$_3$S$_2$: Calcd. (%): C, 36.59; H, 3.69; N, 25.61. Found (%): C, 36.47; H, 3.72; N, 25.21.

(2) The same procedure as in above (1) was repeated, except that other acids were substituted for the methanesulfonic acid to obtain the following results:

| Acid | Amount used (g) | Reaction conditions Reaction temp. (°C.) | Reaction time (hr) | Yield (%) |
|---|---|---|---|---|
| Conc. sulfuric acid | 6.57 | 50 | 1.5 | 84.5 |
| Trifluoromethane-sulfonic acid | 9.0 | 50 | 1 | 87.7 |
| p-Toluenesulfonic acid | 10.3 | 50 | 1.5 | 78.5 |
| Chlorosulfuric acid | 3.5 | 50 | 1 | 76.2 |
| Fluorosulfuric acid | 3.0 | Room temp. | 1.5 | 84.3 |

(3) In above (1), an aqueous ammonium acetate solution (0.77 g of ammonium acetate/4 ml of water) and 3.3 ml of 12 N hydrochloric acid were added to the reaction mixture after the completion of the reaction, and the resulting mixture was stirred at 15° C. for 2 hrs, after which the thus precipitated crystals were collected by filtration, washed with two 5-ml portions of acetone, and then dried to obtain 2.44 g (yield 67.0%) of 7-amino-3-[5-(1-methyl-1,2,3,4-tetrazolyl)thiomethyl]-$\Delta^3$-cephem-4-carboxylic acid hydrochloride having a melting point of 184° to 186° C. (decomp.).

IR (KBr) cm$^{-1}$: $\nu_{C=O}$ 1770, 1710.

NMR (D$_2$O+CF$_3$CO$_2$D): Identical with standard sample.

Elementary analysis for C$_{10}$H$_{13}$N$_6$O$_3$S$_2$Cl: Calcd. (%): C, 32.91; H, 3.59; N, 23.03. Found (%): C, 32.55; H, 3.48; N, 22.73.

EXAMPLE 2

In 80 ml of 0.1 N perchloric acid solution in acetic acid were dissolved 0.54 g of 7-aminocephalosporanic acid and 0.25 g of 5-mercapto-1-methyl-1H-tetrazole, and the solution was sujected to reaction at 50°-55° C. for 2.5 hrs. After the completion of the reaction, the solvent was removed by distillation under reduced pressure. The residue was dissolved in 10 ml of water.

To the resulting aqueous solution was dropwise added conc. aqueous ammonia with ice-cooling, and thereafter, the pH of the solution was adjusted to 3.5, after which the solution was stirred for 15 min. The thus precipitated crystals were collected by filtration, washed with 2 ml of water and 3 ml of methanol in this order, and then dried to obtain 0.53 g (yield 80.8%) of 7-amino-3-[5-(1-methyl-1,2,3,4-tetrazolyl)thiomethyl]$\Delta^3$-cephem-4-carboxylic acid having a melting point of 224° to 226° C. (decomp.). The IR and NMR of the product were identical with those of standard sample.

Example 3

In 13.5 ml of acetic acid were dissolved 1.36 g of 7-aminocephalosporanic acid and 0.58 g of 5-mercapto-1-methyl-1H-tetrazole, and 3.9 g of anhydrous stannic chloride was added to the suspension to form a solution. This solution was subjected to reaction at 50° C. for 1.5 hrs, after which the solvent was removed by distillation under reduced pressure. To the residue was added 10 ml of water, and 28% by weight aqueous ammonia was further added with ice-cooling to adjust the pH of the solution to 7.5. The thus precipitated crystals were collected by filtration, washed with 5 ml of water and 5 ml of acetone in this order, and then dried to obtain 1.28 g (yield 78.0%) of 7-amino-3-[5-(1-methyl-1,2,3,4-tetrazolyl)thiomethyl]-$\Delta^3$-cephem-4-carboxylic acid.

EXAMPLE 4

In 3 ml of acetic acid were suspended 0.27 g of 7-aminocephalosporanic acid and 0.12 g of 5-mercapto-1-methyl-1H-tetrazole, and 1.36 g of anhydrous zinc chloride was added to the suspension to form a solution. This solution was subjected to reaction at 50° C. for 4 hrs, and then diluted with 3 ml of water. The pH of the solution was adjusted to 3.8 with 28% by weight aqueous ammonia with ice-cooling. The thus precipitated crystals were collected by filtration, washed with 2 ml of 0.1 N hydrochloric acid, 2 ml of water and 1 ml of acetone in this order, and then dried to obtain 0.26 g (yield 79.2%) of 7-amino-3-[5-(1-methyl-1,2,3,4-tetrazolyl)thiomethyl]-$\Delta^3$-cephem-4-carboxylic acid.

The IR, NMR and melting point of the product were identical with those of standard sample.

When 3.2 g of zinc bromide was substituted for the zinc chloride, the yield was 77.3%.

EXAMPLE 5

In 15 ml of acetic acid were suspended 1.36 g of 7-aminocephalosporanic acid and 0.58 g of 5-mercapto-1-methyl-1H-tetrazole, and 0.48 g of methanesulfonic acid was added to the suspension to form a solution. To this solution was added 6.80 g of anhydrous zinc chloride, and the resulting mixture was subjected to reaction at 50° C. for 4 hrs. After the completion of the reaction, the reaction mixture was diluted with 15 ml of water, after which the pH thereof was adjusted to 3.8 with 28% by weight aqueous ammonia with ice-cooling. The thus precipitated crystals were collected by filtration, washed with 10 ml of 0.1 N hydrochloric acid, 10 ml of water and 5 ml of acetone in this order, and then dried to obtain 1.35 g (yield 82.3%) of 7-amino-3-[5-(1-methyl-1,2,3,4-tetrazolyl)thiomethyl]-$\Delta^3$-cephem-4-carboxylic acid.

The IR, NMR and melting point of the product were identical with those of standard sample.

EXAMPLE 6

In 5 ml of acetic acid were suspended 0.305 g of p-toluenesulfonic acid salt of diphenylmethyl 7-aminocephalosporanate and 0.058 g of 5-mercapto-1-methyl-1H-tetrazole, and 0.45 g of trifluoromethanesulfonic acid was added to the suspension to form a solution. This solution was subjected to reaction at 50° C. for 1.5 hrs, after which the solvent was removed by distillation under reduced pressure. To the resulting residue were added 2.5 ml of water and 2.5 ml of acetone and the resulting mixture was stirred with ice-cooling for 30 min. Subsequently, 28% by weight aqueous ammonia was added thereto to adjust the pH thereof to 4.0. The thus precipitated crystals were collected by filtration, washed with 3 ml of water and 3 ml of acetone in this order, and then dried to obtain 0.127 g (yield 77.2%) of 7-amino-3-[5-(1-methyl-1,2,3,4-tetrazolyl)thiomethyl]-$\Delta^3$-cephem-4-carboxylic acid.

The IR, NMR and melting point of the product were identical with those of standard sample.

EXAMPLE 7

In 8 ml of acetic acid were suspended 0.796 g of sodium 7-(2-hydroxybenzylideneamino)cephalosporanate and 0.232 g of 5-mercapto-1-methyl-1H-tetrazole, and 1.80 g of trifluoromethanesulfonic acid was added to the suspension to form a solution. This solution was subjected to reaction at room temperature for 3 hrs. With ice-cooling, 1 ml of water and 1.5 ml of 12 N hydrochloric acid were added to the reaction mixture, and the resulting mixture was stirred at room temperature for 2 hrs. The thus precipitated crystals were collected by filtration, washed with two 1-ml portions of acetic acid and two 3-ml portions of acetone in this order, and then dried to obtain 0.503 g (yield 69.0%) of 7-amino-3-[5-(1-methyl-1,2,3,4-tetrazolyl)thiomethyl]-$\Delta^3$-cephem-4-carboxylic acid hydrochloride.

The IR, NMR and melting point of the product were identical with those of standard sample.

EXAMPLE 8

(1) Into 6.8 ml of acetonitrile was gradually dropped 0.58 g of trifluoromethanesulfonic acid, and to the solution were added 0.58 g of 5-mercapto-1-methyl-1H-tetrazole and 1.36 g of 7-aminocephalosporanic acid in this order to form a solution. The resulting solution was heated to 30° C., at which temperature reaction was effected for 60 min., after which the reaction mixture was cooled with ice and 5.7 ml of water was gradually added thereto. The pH of the solution was adjusted to 3.9 with 28% by weight aqueous ammonia and the solution was subjected to stirring at the same temperature for 2 hrs. The thus precipitated crystals were collected by filtration, washed with two 1-ml portions of water and two 1-ml portions of acetone in this order, and then dried to obtain 1.50 g (yield 91.5%) of 7-amino-3-[5-1-methyl-1,2,3,4-tetrazolyl)thiomethyl]-$\Delta^3$-cephem-4-carboxylic acid.

The IR, NMR and melting point of the product were identical with those of standard sample.

(2) The same reaction as above was effected, and to the reaction mixture were added dropwise 0.84 ml of 12 N hydrochloric acid and 0.68 ml of water in this order with ice-cooling, after which the resulting mixture was stirred for 3 hrs. The thus precipitated crystals were collected by filtration, washed with two 2-ml portions of acetonitrile and two 3-ml portions of acetone in this order, and then dried to obtain 1.64 g (yield 90.0%) of 7-amino-3-[5-(1-methyl-1,2,3,4-tetrazolyl)thiomethyl]-$\Delta^3$-cephem-4-carboxylic acid hydrochloride.

The IR, NMR and melting point of the product were identical with those of standard sample.

(3) When propionitrile was substituted for the acetonitrile in above (1), the yield was 88.4%.

(4) When sulfolane was substituted for the acetonitrile in above (1), the yield was 89.6%.

(5) When nitromethane was substituted for the acetonitrile in above (1), the yield was 84.3%.

EXAMPLE 9

In 27 ml of acetonitrile were suspended 2.72 g of 7-aminocephalosporanic acid and 1.16 g of 5-mercapto-1-methyl-1H-tetrazole, and 9.75 g of conc. sulfuric acid was gradually added thereto with ice-cooling to form a solution. This solution was subjected to reaction at 30° C. for 1 hr, and the reaction mixture was cooled to 5° C., and then gradually added to 60 ml of water with ice-cooling. The pH of the solution was adjusted to 3.7 with 28% by weight aqueous ammonia, and 30 ml of water was further added thereto. The resulting solution was stirred at the same temperature for 1 hr. The thus precipitated crystals were collected by filtration, washed with two 15-ml portions of water and three 10-ml portions of acetone in this order, and thereafter dried to obtain 2.93 g (yield 89.3%) of 7-amino-3-[5-(1-methyl-1,2,3,4-tetrazolyl)thiomethyl]-$\Delta^3$-cephem-4-carboxylic acid.

The IR, NMR and melting point of the product were identical with those of standard sample.

EXAMPLE 10

In 6.8 ml of acetonitrile were suspended 1.36 g of 7-aminocephalosporanic acid and 0.60 g of 5-mercapto-1-methyl-1H-tetrazole, and 3.50 g of conc. sulfuric acid was gradually added thereto with ice-cooling to form a solution. This solution was subjected to reaction at 30° C. for 75 min, after which 1.7 ml of 12 N hydrochloric acid and 2.0 ml of water were dropped thereinto in this order while keeping the same temperature. The resulting mixture was cooled to 15° C., and allowed to stand at 10° to 15° C. for 2.5 hrs to precipitate crystals. The precipitated crystals were collected by filtration, washed with two 5-ml portions of acetonitrile and two 5-ml portions of acetone in this order, and thereafter dried to obtain 1.51 g (yield 83.0%) of 7-amino-3-[5-(1-methyl-1,2,3,4-tetrazolyl)thiomethyl]-$\Delta^3$-cephem-4-carboxylic acid hydrochloride.

The IR, NMR and melting point of the product were identical with those of standard sample.

EXAMPLE 11

In 10 ml of acetic acid were suspended 1.36 g of 7-aminocephalosporanic acid and 0.58 g of 5-mercapto-1-methyl-1H-tetrazole, and 6.6 g of stannic bromide was added thereto to form a solution. This solution was subjected to reaction at 50° C. for 2 hrs. The reaction mixture was diluted with 10 ml of water, and 28% by weight aqueous ammonia was added thereto with ice-cooling to adjust the pH thereof to 3.8. The thus precipitated crystals were collected by filtration, and dissolved in 10 ml of 50% by weight aqueous methanol solution by addition of 28% by weight aqueous ammonia. A small amount of insolubles were removed by filtration, after which the pH of the solution was adjusted to 3.8 with 6 N hydrochloric acid. The thus precipitated crystals were collected by filtration, washed with two 5-ml portions of water and two 5-ml portions of acetone in this order, and thereafter dried to obtain 1.28 g (yield 78.2%) of 7-amino-3-[5-(1-methyl-1,2,3,4-tetrazolyl)thiomethyl]-$\Delta^3$-cephem-4-carboxylic acid.

EXAMPLE 12

In 10 ml of acetic acid were suspended 1.36 g of 7-aminocephalosporanic acid and 0.60 g of 5-mercapto-1-methyl-1H-tetrazole, and 8.9 g of pyrophosphoric acid was added to the suspension, after which the resulting mixture was subjected to reaction at 45° to 50° C. for 10 hrs. After the completion of the reaction, the reaction mixture was poured into 10 ml of iced water, and the pH thereof was adjusted to 3.8 with 28% by weight of aqueous ammonia. The thus precipitated crystals were collected by filtration, washed with two 5-ml portions of water and two 5-ml portions of acetone in this order, and thereafter dried to obtain 1.17 g (yield 70.9%) of 7-amino-3-[5-(1-methyl-1,2,3,4-tetrazolyl)thiomethyl]-$\Delta^3$-cephem-4-carboxylic acid.

EXAMPLE 13

In 7.0 ml of acetic acid were suspended 1.35 g of 7-aminocephalosporanic acid and 0.60 g of 5-mercapto-1-methyl-1H-tetrazole, and 0.93 ml of 100% magic acid (fluorosulfuric acid:antimony pentafluoride = 1:1 by mole) was added to the suspension with ice-cooling, after which the mixture was subjected to reaction at 30° C. for 3 hrs. After the completion of the reaction, the reaction mixture was poured into 35 ml of iced water, and the pH of the resulting solution was adjusted to 3.7 with conc. aqueous ammonia, after which the solution was stirred with ice-cooling for 1 hr. The thus precipitated crystals were collected by filtration, washed with 10 ml of water and 10 ml of acetone in this order, and thereafter dried to obtain 1.34 g (yield 82.0%) of 7-amino-3-[5-(1-methyl-1,2,3,4-tetrazolyl)thiomethyl]-$\Delta^3$-cephem-4-carboxylic acid.

EXAMPLE 14

The following objective compounds are obtained in yields of 65 to 90% under substantially the same conditions as in Examples 1 to 13 by using 7-aminocephalosporanic acid, a suitable thiol compound represented by formula (II), an acid selected from sulfuric acid, pyrophosphoric acid, perchloric acid, chlorosulfuric acid, pyrosulfuric acid, fluororsulfuric acid, magic acid, $FSO_3H$—$AsF_5$, $CF_3SO_3H$—$SbF_5$, $H_2SO_4$—$SO_3$, methanesulfonic acid, trifluoromethanesulfonic acid, p-toluenesulfonic acid, zinc chloride, zinc bromide, stannic chloride, and stannic bromide, and a solvent selected from acetonitrile and acetic acid:

7-Amino-3-[2-(1,3,4-thiadiazolyl)thiomethyl]-$\Delta^3$-cephem-4-carboxylic acid.

7-Amino-3-[5-(1-sulfomethyl-1,2,3,4-tetrazolyl)thiomethyl]-$\Delta^3$-cephem-4-carboxylic acid.

7-Amino-3-[2-(5-methyl-1,3,4-oxadiazolyl)thiomethyl]-$\Delta^3$-cephem-4-carboxylic acid.

7-Amino-3-[2-(5-methyl-1,3-thiazolyl)thiomethyl]-$\Delta^3$-cephem-4-carboxylic acid.

7-Amino-3-[2-(5-methyl-1,3-oxazolyl)thiomethyl]-$\Delta^3$-cephem-4-carboxylic acid.

7-Amino-3-[2-(1-methyl-1,3,4-triazolyl)thiomethyl]-$\Delta^3$-cephem-4-carboxylic acid.

7-Amino-3-[2-(1,3-thiazolyl)thiomethyl]-$\Delta^3$-cephem-4-carboxylic acid.

7-Amino-3-[2-(5-amino-1,3,4-thiadiazolyl)-thiomethyl]-$\Delta^3$-cephem-4-carboxylic acid.

7-Amino-3-[2-(5-phenyl-1,3,4-thiadiazolyl)-thiomethyl]-$\Delta^3$-cephem-4-carboxylic acid.

7-Amino-3-[5-(3-methyl-1,2,4-thiadiazolyl)-thiomethyl]-$\Delta^3$-cephem-4-carboxylic acid.

7-Amino-3-[5-(1,2,3,4-thiatriazolyl)-thiomethyl]-$\Delta^3$-cephem-4-carboxylic acid.

7-Amino-3-[2-(5-methyl-1,3,4-triazolyl)-thiomethyl]-$\Delta^3$-cephem-4-carboxylic acid.

7-Amino-3-[2-(1,5-dimethyl-1,3,4-triazolyl)-thiomethyl]-$\Delta^3$-cephem-4-carboxylic acid.

7-Amino-3-[2-(imidazolyl)thiomethyl]-$\Delta^3$-cephem-4-carboxylic acid.

7-Amino-3-[4-(5-ethoxycarbonyl-1,2,3-triazolyl)thiomethyl]-$\Delta^3$-cephem-4-carboxylic acid.

7-Amino-3-[4-(5-carboxyl-1,2,3-triazolyl)-thiomethyl]-$\Delta^3$-cephem-4-carboxylic acid.

7-Amino-3-[2-(5-ethoxycarbonylmethyl-1,3,4-triazolyl)thiomethyl]-$\Delta^3$-cephem-4-carboxylic acid.

7-Amino-3-[5-(1-carboxymethyl-1,2,3,4-tetrazolyl)thiomethyl]-$\Delta^3$-cephem-4-carboxylic acid.

7-Amino-3-{5-[2-(2-carbamoyl)ethyl-1,2,3,4-tetrazolyl]thiomethyl}-$\Delta^3$-cephem-4-carboxylic acid.

7-Amino-3-[2-(5-carboxymethyl-1,3,4-thiadiazolyl)thiomethyl]-$\Delta^3$-cephem-4-carboxylic acid.

7-Amino-3-{5-[1-(2-sulfamoyl)ethyl-1,2,3,4-tetrazolyl]thiomethyl}-$\Delta^3$-cephem-4-carboxylic acid.

7-Amino-3-{5-[1-(2-dimethylamino)ethyl-1,2,3,4-tetrazolyl]thiomethyl}-$\Delta^3$-cephem-4-carboxylic acid.

7-Amino-3-{5-[1-(2-diethylamino)ethyl-1,2,3,4-tetrazolyl]thiomethyl}-$\Delta^3$-cephem-4-carboxylic acid.

7β-Amino-7α-methoxy-3-[2-(5-methyl-1,3,4-thiadiazolyl)thiomethyl]-Δ³-cephem-4-carboxylic acid.

7β-Amino-7α-methoxy-3-[5-(1-methyl-1,2,3,4-tetrazolyl)thiomethyl]-Δ³-cephem-4-carboxylic acid.

7-Amino-3-[5-(1-vinyl-1,2,3,4-tetrazolyl)thiomethyl]-Δ³-cephem-4-carboxylic acid.

7-Amino-3-{5-[2-(2-dimethylaminoethyl)-1,2,3,4-tetrazolyl]thiomethyl}-Δ³-cephem-4-carboxylic acid.

7-Amino-3-[2-(5-ethyl-1,3,4-thiadiazolyl)thiomethyl]-Δ³-cephem-4-carboxylic acid.

7-Amino-3-[5-(1-phenyl-1,2,3,4-tetrazolyl)thiomethyl]-Δ³-cephem-4-carboxylic acid.

7-Amino-3-[2-(benzoxazolyl)thiomethyl]-Δ³-cephem-4-carboxylic acid.

7-Amino-3-[5-(1,2,3-triazolyl)thiomethyl]-Δ³-cephem-4-carboxylic acid.

7-Amino-3-[2-(benzimidazolyl)thiomethyl]-Δ³-cephem-4-carboxylic acid.

7-Amino-3-propylthiomethyl-Δ³-cephem-4-carboxylic acid.

7-Amino-3-phenylthiomethyl-Δ³-cephem-4-carboxylic acid.

7-Amino-3-[5-(1-ethyl-1,2,3,4-tetrazolyl)thiomethyl]-Δ³-cephem-4-carboxylic acid.

7-Amino-3-[5-(1-carbamoylmethyl-1,2,3,4-tetrazolyl)thiomethyl]-Δ³-cephem-4-carboxylic acid.

7-Amino-3-{5-[1-(2-hydroxyethyl)-1,2,3,4-tetrazolyl]thiomethyl}-Δ³-cephem-4-carboxylic acid.

7-Amino-3-(ethoxycarbonylmethylthiomethyl)-Δ³-cephem-4-carboxylic acid.

7-Amino-3-(carboxymethylthiomethyl)-Δ³-cephem-4-carboxylic acid.

7-Amino-3-{5-[1-(2-aminoethyl)-1,2,3,4-tetrazolyl]thiomethyl}-Δ³-cephem-4carboxylic acid.

7-Amino-3-[5-(1,2,3,4-tetrazolyl)thiomethyl]-Δ³-cephem-4-carboxylic acid.

7-Amino-3-[5-(1-methoxycarbonylmethyl-1,2,3,4-tetrazolyl)thiomethyl]-Δ³-cephem-4-carboxylic acid.

7-Amino-3-[2-(5-methyl-1,3,4-thiadiazolyl)thiomethyl]-Δ³-cephem-4-carboxylic acid.

7-Amino-3-[2-(5-ethyl-1,3,4-thiadiazolyl)thiomethyl]-Δ³-cephem-4-carboxylic acid.

What is claimed is:

1. A process for producing a 7-(substituted)-amino-3-substituted thiomethyl-Δ³-cephem-4-carboxylic acid represented by the formula,

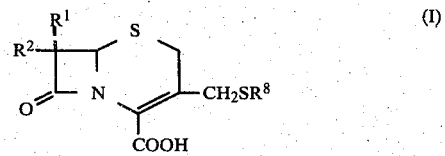 (I)

wherein R¹ is a hydrogen atom or a C₁₋₄ alkyloxy group; R² is an amino group or a protected amino group represented by the formula,

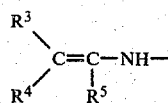

in which R³, R⁴ and R⁵, which may be identical or different, are hydrogen atoms or conventional cephalosporin substituents which do not participate in the reaction, or by the formula,

in which R⁶ and R⁷, which may be identical or different, are hydrogen atoms or conventional cephalosporin substituents which do not participate in the reaction; and R⁸ is a moiety of a compound of the formula R⁸SH, where SR⁸ is a conventional 3-position cephalosporin thio substituent, or said compound (I) in which the carboxyl group is protected by a conventional cephalosporin carboxy protective group or a conventional cephalosporin salt thereof, which comprises reacting a cephalosporanic acid represented by the formula,

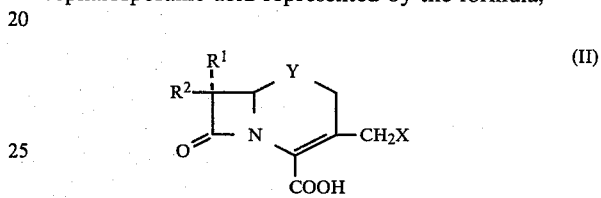 (II)

wherein R¹ and R² have the same meanings as defined above; X is carboxylic acyloxy or carbamoyloxy group or one of said groups substituted by a conventional cephalosporin substituent; >Y is >S or >S→0; or said compound (II) in which the carboxyl group is protected by a conventional cephalosporin carboxy protective group or a conventional cephalosporin salt thereof, with a thiol compound represented by the formula,

R⁸—SH (III)

wherein R⁸ has the same meanings as defined above, or a salt thereof with a compound forming a conventional cephalosporin salt, in a non-aqueous organic solvent at a temperature of −20° to 80° C. in the presence of a protonic acid selected from pyrophosphoric acid, pyrosulfuric acid, sulfuric acids, sulfonic acids or super acids, or a Lewis acid selected from zinc halides or tin halides or complex compound of said Lewis acid, said complex compound being a complex compound of said Lewis acid with dialkyl ethers, amines, fatty acids, nitriles, carboxylic esters or phenols.

2. A process according to claim 1, wherein the protonic acid is pyrophosphoric acid, a sulfuric acid, a sulfonic acid or a super acid.

3. A process according to claim 1, wherein the protonic acid or Lewis acid is pyrophosphoric acid, sulfuric acid, chlorosulfuric acid, fluorosulfuric acid, methanesulfonic acid, trifluoromethanesulfonic acid, p-toluenesulfonic acid, magic acid (FSO₃H—SbF₅), perchloric acid, zinc chloride, zinc bromide, stannic chloride, or a stannic bromide.

4. A process according to claim 3, wherein the organic solvent is an aliphatic saturated mono- or di-carboxylic acid, a nitrile, a nitroalkane or a sulfolane.

5. A process according to claim 4, wherein R² is an amino group.

6. A process according to claim 4, wherein R² is a group represented by the formula,

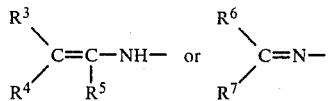

in which $R^3$, $R^4$, $R^5$, $R^6$ and $R^7$ have the same meanings as defined in claim 1.

7. A process according to claim 5, wherein $>Y$ is $>S$.

8. A process according to claim 5, wherein $>Y$ is $>S\rightarrow O$.

9. A process according to claim 5, wherein $R^1$ is a hydrogen atom.

10. A process according to claim 5, wherein $R^1$ is a methoxy group.

11. A process according to any one of claims 1, 2, 3, 4, 5, 6, 7, 8, 9 and 10 wherein $R^8$ is an oxazolyl, thiazolyl, isoxazolyl, isothiazolyl, imidazolyl, pyrazolyl, pyridyl, pyrazinyl, pyrimidinyl, pyridazinyl, quinolyl, isoquinolyl, quinazolyl, indolyl, indazolyl, oxadiazolyl, thiadiazolyl, triazolyl, thiatriazolyl, tetrazolyl, triazinyl, benzimidazolyl, benzoxazolyl, benzothiazolyl, triazolopyridyl, purinyl, pyridine-1-oxide-2-yl, pyridazine-1-oxide-6-yl, tetrazolopyridazinyl, tetrazolopyrimidinyl, triazolopyridazinyl, thiadiazolopyridazinyl or triazolopyridazinyl which may be substituted by at least one substituent selected from halogen, $C_{1-4}$ alkyl, phenyl, hydroxyl, mercapto, $C_{1-4}$ alkoxy, $C_{1-4}$ alkylthio, nitro, cyano, cyano-$C_{1-4}$ alkyl, amino, $C_{1-4}$ alkylamino, di-$C_{1-4}$ alkylamino, $C_{1-8}$ acylamino, $C_{1-8}$ acyl, $C_{1-8}$ acyloxy, carboxyl, carbamoyl, amino-$C_{1-4}$ alkyl, N-$C_{1-4}$ alkylamino-$C_{1-4}$ alkyl, N,N-di-$C_{1-4}$ alkylamino-$C_{1-4}$ alkyl, hydroxy-$C_{1-4}$ alkyl, $C_{1-4}$ alkoxy-$C_{1-4}$ alkyl, carboxyl-$C_{1-4}$ alkyl, sulfo-$C_{1-4}$ alkyl, sulfo, sulfamoyl-$C_{1-4}$ alkyl, sulfamoyl, carbamoyl-$C_{1-4}$ alkyl, $C_{2-4}$ alkenyl, carbamoyl-$C_{2-4}$ alkenyl, N-$C_{1-4}$ alkylcarbamoyl, N,N-di-$C_{1-4}$ alkylcarbamoyl, $C_{1-8}$ acyl-$C_{1-4}$ alkyl, N-$C_{1-4}$ alkylcarbamoyl-$C_{1-4}$ alkyl, or N,N-di-$C_{1-4}$ alkylcarbamoyl-$C_{1-4}$ alkyl.

12. A process according to claim 11, wherein $R^8$ is 5-(1-methyl-1,2,3,4-tetrazolyl), 2-(1,3,4-thiadiazolyl) or 5-(2-methyl-1,3,4-thiadiazolyl) group.

13. A process according to claim 12, wherein $R^8$ is 5-(1-methyl-1,2,3,4-tetrazolyl) group.

14. A process according to claim 13, wherein the reaction is effected at a temperature of $-20°$ to $80°$ C.

15. A process according to claim 12, wherein the protonic acid is pyrophosphoric acid, sulfuric acid, chlorosulfuric acid, fluorosulfuric acid, methanesulfonic acid, trifluoromethanesulfonic acid, p-toluenesulfonic acid, magic acid, or perchloric acid.

16. A process according to claim 1 wherein 7-aminocephalosporanic acid, 5-mercapto-1-methyl-1H-tetrazole and a protonic acid or a Lewis acid are admixed with non-aqueous acetic acid or acetonitrile to form a mixture which is allowed to react at $-20°$ C. to $80°$ C. to form 7-amino-3-[5-(1-methyl-1,2,3,4-tetrazolyl)-thiomethyl]-$\Delta^3$-cephem-4-carboxylic acid, the protonic acid being pyrophosphoric acid, sulfuric acid, chlorosulfuric acid, fluorosulfuric acid, methanesulfonic acid trifluoromethanesulfonic acid, p-toluenesulfonic acid, magic acid ($FSO_3H$—$SbF_5$) or perchloric acid and the Lewis acid being zinc chloride, zinc bromide, stannic chloride or stannic bromide.

17. A process according to claim 1, wherein the p-toluenesulfonic acid salt of diphenylmethyl 7-aminocephalosporanate, 5-mercapto-1-methyl-1H-tetrazole and trifluoromethanesulfonic acid are admixed with non-aqueous acetic acid to form a mixture which is allowed to react at $-20°$ C. to $80°$ C. to form a product from which 7-amino-3-[5-(1-methyl-1,2,3,4-tetrazolyl)thiomethyl]-$\Delta^3$-cephem-4-carboxylic acid is recovered.

18. A process according to claim 1 wherein sodium 7-(2-hydroxybenzylideneamino) cephalosporanate, 5-mercapto-1-methyl-1H-tetrazole and trifluoromethanesulfonic acid are admixed with non-aqueous acetic acid to form a mixture which is allowed to react at $-20°$ C. to $80°$ C. to form a product from which 7-amino-3-[5-(1-methyl-1,2,3,4-tetrazolyl)thiomethyl]-$\Delta^3$-cephem-4-carboxylic acid hydrochloride is recovered.

19. A process according to claim 6 wherein $>Y$ is $>S$.

20. A process according to claim 6 wherein $>Y$ is $>S\rightarrow O$.

21. A process according to claim 6 wherein $R'$ is a hydrogen atom.

22. A process according to claim 6 wherein $R'$ is a methoxy group.

23. A process according to claim 11 wherein the reaction is effected at a temperature of $-20°$ to $80°$ C.

* * * * *